United States Patent
Helftenbein

(10) Patent No.: US 7,282,371 B2
(45) Date of Patent: Oct. 16, 2007

(54) CONTAINER FOR NUCLEIC ACID ANALYSIS

(75) Inventor: Elke Helftenbein, Stuttgart (DE)

(73) Assignee: Preanalytix GmbH, Hombrechitkon (CH)

(*) Notice: Subject to any disclaimer, the term of this patent is extended or adjusted under 35 U.S.C. 154(b) by 0 days.

(21) Appl. No.: 10/204,038

(22) PCT Filed: Feb. 15, 2001

(86) PCT No.: PCT/EP01/01705

§ 371 (c)(1),
(2), (4) Date: Nov. 25, 2002

(87) PCT Pub. No.: WO01/60517

PCT Pub. Date: Aug. 23, 2001

(65) Prior Publication Data

US 2003/0143566 A1    Jul. 31, 2003

(30) Foreign Application Priority Data

Feb. 15, 2000 (DE) .................. 100 06 662

(51) Int. Cl.
G01N 1/18 (2006.01)
C12Q 1/68 (2006.01)

(52) U.S. Cl. ............... 436/178; 436/174; 436/176; 436/177; 435/6; 435/287.2; 536/25.4

(58) Field of Classification Search ............ 422/61, 422/99, 102, 939; 436/174, 176, 177, 178, 436/8, 18; 435/6, 287.2, 260; 536/25.4
See application file for complete search history.

(56) References Cited

U.S. PATENT DOCUMENTS

| 5,346,994 A | 9/1994 | Chomczynski |
| 5,667,963 A | 9/1997 | Smith et al. |
| 6,027,886 A | 2/2000 | Leying et al. |
| 6,218,531 B1 | 4/2001 | Ekenberg |
| 6,231,815 B1 | 5/2001 | Bainczyk et al. |
| 6,274,386 B1 | 8/2001 | Harttig |
| 6,602,718 B1* | 8/2003 | Augello et al. ............ 436/176 |
| 6,617,170 B2* | 9/2003 | Augello et al. ............ 436/176 |
| 6,821,789 B2* | 11/2004 | Augello et al. ............ 436/176 |
| 7,067,287 B1* | 6/2006 | Sakurai et al. ............ 435/91.1 |
| 2002/0068821 A1* | 6/2002 | Gundling ................ 536/23.1 |

FOREIGN PATENT DOCUMENTS

| EP | 0 389 063 A | 9/1990 |
| EP | 0 818 542 A | 1/1998 |
| JP | 2002-522092 | 7/2002 |
| WO | WO97 05248 A | 2/1997 |
| WO | WO98 32877 | 7/1998 |
| WO | WO 00 09746 A | 2/2000 |

OTHER PUBLICATIONS

Lozano, M.E. et al., "A simple nucleic acid amplification assay for the rapid detection of Junin virus in whole blood samples," Virus Research, Amsterdam, NL, Bd. 27, 1993, Seiten 37-53.

* cited by examiner

Primary Examiner—Maureen M. Wallenhorst

(57) ABSTRACT

The present invention relates to a receptacle for receiving samples, containing a nucleic-acid stabilizing solution and a nucleic-acid-binding solid phase. The receptacle is especially suited for the withdrawal of blood to be examined for nucleic acid.

31 Claims, 5 Drawing Sheets

CONTAINER FOR NUCLEIC ACID ANALYSIS

Figure 1:
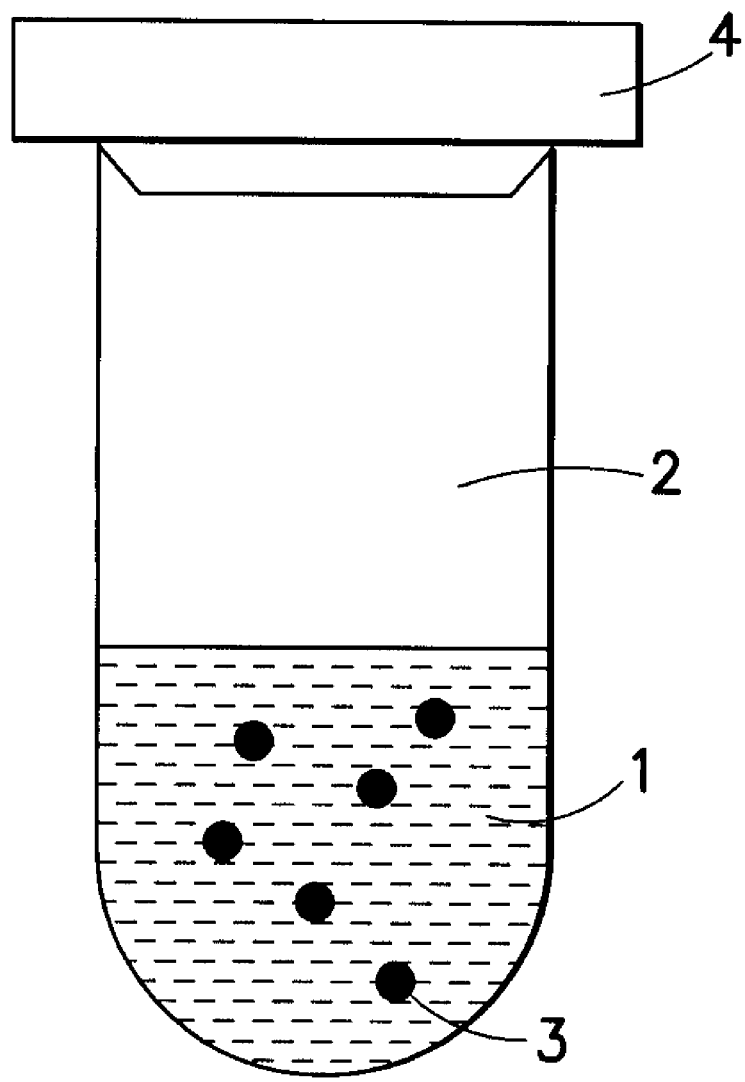

The present application is a 35 U.S.C. §371 national phase application from, and claims priority to, international application PCT/EP01/01705, filed Feb. 15, 2001, which claims priority to German patent application No. 100 06 662.3, filed Feb. 15, 2000, which applications are incorporated herein in their entirety by reference.

The present invention relates to a receptacle for receiving samples, preferably for the withdrawal of blood, whereby the withdrawn blood is to be applied especially for the stabilization, isolation and analytics of nucleic acids.

During the withdrawal, the blood is conventionally collected in receptacles already containing anticoagulants, such as heparin, citrate or EDTA. It is thereby prevented that the blood coagulates. Blood samples obtained in this way can be stored at suitable temperatures for longer periods of time. Said kind of obtaining blood, however, involves considerable drawbacks if nucleic acids such as mRNA or DNA are to be analyzed. For such purposes, the nucleic acids contained in the sample should best be stabilized at the time of withdrawal, in other words, the degradation of the present nucleic acids, but also the new synthesis of mRNA should be prevented.

Said objective relating to the stable storage of the nucleic acids contained in the sample material from the moment of withdrawal has so far practically been impossible to achieve in view of the storage of blood for the following reasons:

Cells contain nucleases, i.e. enzymes, which destroy the nucleic acids as soon as they come into contact with their substrates (RNA, DNA). The effect of cellular and extracellular nucleases is normally under physiological control, as long as the cells are in their normal environment. The withdrawal of blood results in more or less strong changes of the nucleic acids contained in the cells. Nucleases are then, within the cells and/or by the lysis of cells, outwardly released. Moreover, nucleic acids are synthesized more or less strongly. Specifically the permanent long-time storage of blood results in the aging and the destruction of the cells.

Another problem involved by the long-time storage of blood samples obtained according to conventional withdrawal methods resides in the strong transformation of the sample material. Such changes, such as the strong lysis of cells may entail that the standard methods for the isolation of nucleic acids no longer work with satisfactory efficiency and reproducibility.

Apart from the problems relating to the stable storage of nucleic acids contained in the sample material, the conventional method of withdrawing blood entails additional difficulties. During the isolation of nucleic acids, the conventional anticoagulants are frequently not separated with enough efficiency, and have a disturbing effect on the subsequent nucleic acid analytics, such as the amplification by means of PCR (polymerase chain reaction). Heparin is, for example, a generally known inhibitor of the PCR.

Finally, the quantitative nucleic acid analytics raises the question as to how the entire process, starting with the withdrawal of the sample until the measurement of the nucleic acid, can be controlled under standardized conditions. Ideally, a standard nucleic acid, defined in terms of quantity and quality, should already be added to the sample material during the withdrawal, so as to subject it to the entire process of withdrawing the sample and determining it. This, too, is impossible with the conventional withdrawal systems.

Another drawback in view of the conventional withdrawal of blood resides in the risk of transmitting infectious material, as, so far, manual process steps are required for the isolation of nucleic acids. A contact with potential infectious germs cannot be precluded.

A method is described in the state of the art, according to which the blood sample is mixed with guanidinium salt directly after the withdrawal from the patient (EP 0 818 542 A1). When using said method, the guanidinium salt is powdery so as to exploit the higher stability of the guanidinium salt. Said method embodies, however, serious disadvantages, since the salt, for example, has to dissolve in the added blood first. The dissolution process depends, in particular, on the temperature and cannot be controlled due to the used nontransparent sample material. The use of a corresponding product for diagnostic/medical purposes is, therefore, extremely problematical.

Nucleases are extremely active enzymes, which can be inhibited only under extremely denaturating conditions. The denaturation depends on the concentration of the dissolved guanidinium salt. According to the method described in EP 0 818 542 an inhibiting concentration of dissolved guanidinium salt is not provided from the very beginning. Thus, the degradation of nucleic acids during the dissolution process takes place in an uncontrolled manner. Furthermore, according to said method, no reducing agents are added, without which an effective inhibition—especially of RNases—is usually not guaranteed.

The sample obtained according to conventional methods can, moreover, not directly be used for the additional isolation of nucleic acids on solid phases. The use of guanidinium salt moreover does not allow the addition of internal nucleic acid standards. Such standards are, however, absolutely necessary for controlling the process and for the exact quantification.

The present invention was based on the technical object to provide a receptacle that does not embody the disadvantages known from the state of the art. In particular, the sample withdrawn with the receptacle is to be capable of being subjected directly to the current nucleic acid analyzing methods, without having to carry out additional steps for processing the samples.

According to the invention said object is provided by a receptacle for receiving a sample, containing a solution for stabilizing nucleic acids, and a solid phase for binding nucleic acids.

Additional preferred embodiments are described in the subsidiary claims.

The receptacle according to the invention has the following advantages: 1. The sample, preferably blood, is lysed at the time of withdrawal already, namely because the withdrawal receptacle already contains a corresponding lysis solution, which is, at the same time, a nucleic-acid-stabilizing solution. 2. The nucleic acid stabilizing solution has the effect that the sample material, especially the nucleic acids contained therein, are stabilized directly after contacting the solution. 3. The nucleic-acid-stabilizing solution is, moreover, selected such that the sample material can directly be used in subsequent isolation methods. 4. The nucleic-acid-stabilizing solution can be separated during the subsequent isolation efficiently enough to prevent an inhibition, for instance, of the PCR. 5. An internal standard may be added to the nucleic-acid-stabilizing solution, which allows the control of the entire process, from the withdrawal of the sample to the detection of nucleic acid. 6. The solid phase contained in the receptacle is particularly suited for an isolation of the nucleic acids bound thereto at a later time.

Moreover, the preferred binding of the nucleic acids to the solid phase facilitates the subsequent isolation, because a first separation of nucleic acid and additional components of the sample already takes place in the receptacle.

The nucleic-acid-stabilizing solution may be selected such that the nucleic acid is bound to the corresponding surface immediately after the cell lysis, or only after the addition of additional reagents. The former case is, for example, given if a glass surface in the presence of a guanidinium salt is provided in advance. The second case can, for instance, be achieved by providing a biotin-coated surface in advance and by subsequently adding streptavidin with nucleic-acid-binding properties.

The receptacle can basically be used for receiving any body liquids. It is, in particular, suited for receiving body liquids containing cellular components, such as bone marrow. Preferably, however, a receptacle for the direct withdrawal of whole blood from a donor is concerned.

The receptacle is preferably formed of a conventional blood withdrawal receptacle (e.g. a small tube), in which a defined volume of a nucleic-acid-stabilizing solution and a nucleic-acid-binding solid phase are contained. The small tube is thereafter preferably provided with a defined low pressure, which allows that only a certain volume of blood is withdrawn. The small tube may be handled according to conventional methods for the withdrawal of blood. The solution contained in the small tube contains, according to its preferred embodiment, the following reagents: a guanidinium salt, e.g. guanidinium thiocyanate, a detergent; e.g Triton-X-100, a reducing agent, e.g dithiothreitol, and a suitable buffer system such as citrate, tris, MES or HEPES. In the described composition, the solution is compatible with the small vacuum tube. The solution can be stored in the small vacuum tube without any problems, without adversely affecting the desired stabilizing function. Particularly for the blood donor the entire system is unproblematic and safe for the withdrawal of blood.

The solution containing the guanidinium salt, which serves as lysis and stabilizing substance, the nucleic-acid-binding solid phase, the buffer substance, the reducing agent and the detergent is stable in storage and transforms the added, freshly withdrawn blood into a material, which is likewise stable in storage and which can directly be used for the additional analysis and, respectively, isolation of nucleic acid.

Guanidinium thiocyanate and/or guanidinium chloride are preferably used as guanidinium salt.

The guanidinium salt is preferably present in a concentration of 1 to 8.0 M.

Tris or citrate are preferably used as buffer substance, whereby the exact pH is preferably adjusted with HCl. Other possible buffers are, however, HEPES, MOPS, MES, citrate and phosphate buffers, such as, for example, PBS.

As solid phase all nucleic-acid-binding materials may be used. Especially suited are glass particles, nucleic-acid-binding polymers, particles coated therewith, nucleic-acid-binding coatings of the withdrawal system or particles coated with silica. Alternatively, the surface of the nucleic-acid-binding solid phase may be coated with specific binding molecules (e.g. streptavidin, oligonucleotides, peptide nucleic acids (PNAs) etc., which interact with marker molecules on the nucleic acid or directly with the nucleic acid. The forming of-the materials only depends on the form of the withdrawal system and the subsequent isolation method. Especially suited are formings which can directly be used afterwards when the nucleic acid is additionally processed.

Especially suited are surfaces being compatible with conventional isolation methods, such as magnetic particles or fleeces.

Suitable solid phases are commercially available, e.g. magnetic particles coated with silica, as are contained in the mRNA Isolation Kit for Blood/Bone Marrow (Roche).

The buffer concentration preferably ranges between 10 and 300 mM, even more preferably between 10 and 100 mM.

Triton-X-100 is preferred as detergent. Other possible detergents are NP-40, Tween 20, Polydocanol or other detergents.

The detergent concentration preferably ranges between 5 and 30% (w/v), even more preferably between 10 and 20% (w/v).

As reducing agent DTT is preferred, whereby, however, also β-mercaptoethanol, TCEP (tris(2-carboxyethyl)phosphine) or other reducing agents can be used.

The preferred cocentration of the reducing agent ranges between 0.1 and 10% (w/v), even more preferred are 0.5 to 2% (w/v).

The pH of the solution preferably ranges between 3.0 and 9.0, even more preferably between 4.0 and 7.5.

The pH of the solution is particularly selected such that, upon the addition of the sample material, a pH-value in the range of 5.0 to 7.5 is adjusted. As it is secured by predefining the low pressure, as to which sample volume is withdrawn, it can be guaranteed by employing a desired buffer concentration or, respectively, a corresponding solution volume in advance, that the desired pH is actually obtained upon the reception of the complete sample volume. Especially preferred is a pH ranging between 6.3 and 6.9 after the reception of the sample.

A specifically preferred solution contains 4.5 M guanidinium thiocyanate, 50 mM tris/HCl, 15% (w/v) Triton-X-100, 100 mM DTT, a solid phase of glass particles or magnetic particles coated with silica, whereby the pH is adjusted such that a pH of 6 to 7.5 is obtained after the addition of blood.

According to an additional preferred embodiment the volume for receiving the blood sample has a low pressure, which can be adjusted such that a previously defined blood volume is sucked into the receptacle, after a blood vessel was punctured. Correspondingly evacuated receptacles are available on the market.

The receptacle containing the withdrawn blood can then immediately be subjected to the additional analytics, or it may be preserved for a longer time period (up to several days or weeks) without any disadvantages for the quality of the sample.

According to the method underlying the present invention the freshly withdrawn blood is directly contacted with the above-described solution in the blood withdrawal receptacle, so that all processes which may change the nucleic acid pattern of the sample are stopped. The nucleic acids may preferably be present in the receptacle already bound to the solid phase, or they may be bound to the solid phase in an additional reaction step.

The data relating to the proven nucleic acids, which are determined later within the scope of the nucleic acid analytics, thus exactly constitute the actual condition at the time of the blood withdrawal, namely in view of the quantities and in view of the types of the nucleic acids.

The withdrawn quantity of blood preferably corresponds to 0.1 to 4 times the quantity of the solution present in the receptacle. The latter preferably amounts to 0.5 to 5.0 ml. Thus, the final concentration of guanidinium salt after the addition of blood preferably ranges between 1.0 and 5 M, preferably between 1.0 and 3.0 M.

The receptacle according to the invention is preferably used for the withdrawal of blood, if the blood sample is meant to be used for the analytics of nucleic acids.

The use of the above-mentioned solution as part of the described withdrawal system alone guarantees the immediate lysis of the cells and the simultaneous stabilization of the sample by the direct inactivation of the nucleases. The so obtained blood sample can surprisingly be stored over several days even at room temperature. The withdrawal system moreover guarantees a non-infectious handling, safe against contamination, namely starting with the withdrawal of the blood, via the isolation of the nucleic acid up to the analytics. According to the conventional methods for the isolation of nucleic acids, so far additional handling steps (such as transferring the withdrawn blood sample into the reagents for the nucleic acid isolation etc.) have always been necessary, which bear an additional risk of infection or contamination of the sample.

The nucleic acid bound to the solid phase can surprisingly be isolated from the sample material in an easy manner, even after a longer storage. The presence of the solid phase during the lysis of the sample entails an immediate binding of the nucleic acids to the surface. Thus, losses in the yield caused, for instance, by the formation of a precipitate, which may occur after a longer storage, are prevented, as the surface with the nucleic acid practically bound therein in a quantitative manner may easily be removed from the system.

The sample obtained with the blood withdrawal system can be subjected to current methods for isolating nucleic acids. When using magnetic particles coated with silica, it is feasible to use current standard methods for isolating nucleic acids (magnetic separation, washing, elution of the nucleic acid).

The present invention, thus, consists of a sample receiving system, which is configured such that the following conditions are fulfilled: 1. Controlled withdrawal of the sample and simultaneous stabilization of the nucleic acids (DNA, RNA) contained in the sample material. 2. Withdrawal of the sample, which can entirely be made without using anticoagulants. 3. Binding the nucleic acids (directly or after an additional process step) to a solid phase contained in the system. 4. The sample obtained with the described system can easily be integrated into existing isolation systems for nucleic acids. 5. The system including the sample contained therein is stable in storage.

In addition, it has surprisingly been found that the sample obtained with the described withdrawal system is stable in storage in the receptacle over a longer time period, without degradation of the nucleic acids.

The following examples will explain the invention.

FIG. 1:
Sample withdrawal receptacle with a nucleic-acid-stabilizing substance 1 (N-sS), defined vacuum 2, containing a solid phase 3 and sealed with septum 4.

Figure 2:
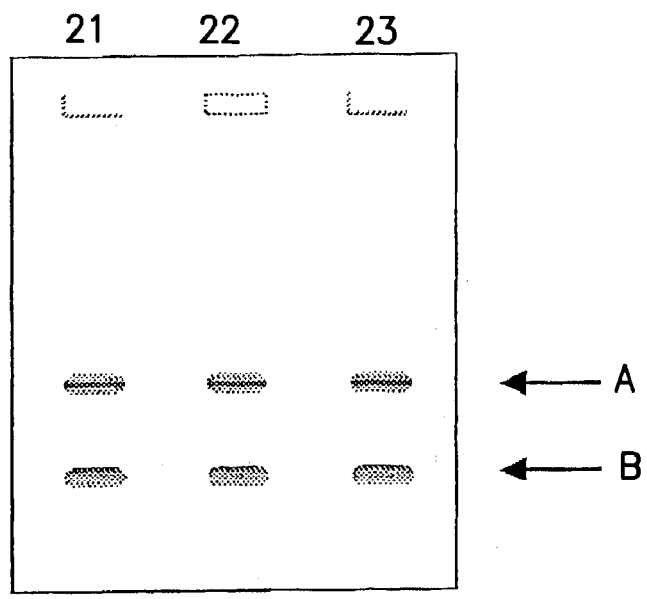

FIG. 2:
Graphical illustration of a gel analysis (1% agarose) of 28S rRNA (represented by A) and 18S rRNA (represented by B) stored in the sample withdrawal receptacle for different periods of time. Column 21: Isolation and separation of the RNA immediately after the withdrawal of the sample (no storage), column 22: Storage for one month at −20° C., column 23: Storage for 6 days at 4° C. The amount of the applied RNA corresponded to a blood volume of 120 µl.

Figure 3:
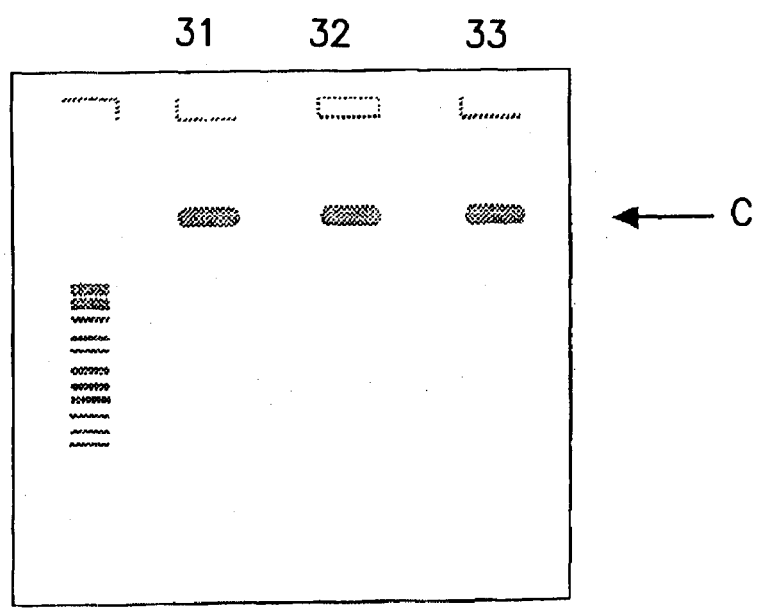

FIG. 3:
Graphical illustration of a gel analysis (1% agarose) of DNA C stored in the sample withdrawal receptacle for different periods of time. Column 31: Isolation immediately after the withdrawal of the sample (no storage), column 32: Storage for one month at −20° C., column 33: Storage for 6 days at 4° C. The amount of the applied RNA corresponded to a blood volume of 10 µl.

Figure 4:
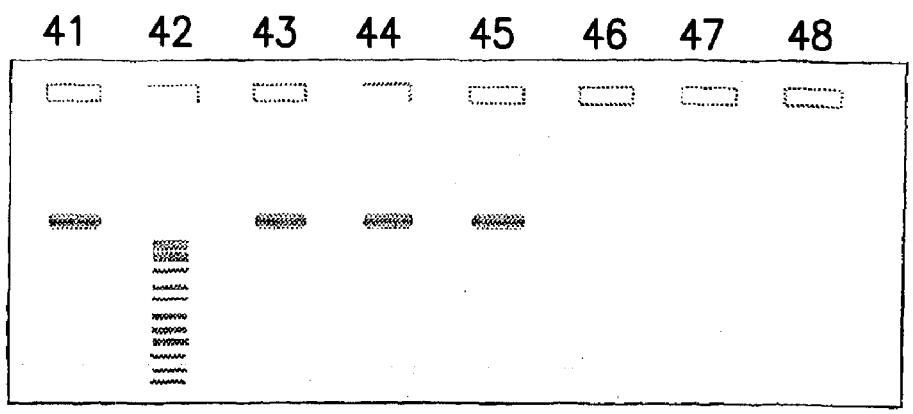

FIG. 4:
Graphical illustration of a gel analysis of isolated MS2-RNA after incubation in serum/stabilizing solution with/without DTT after 180 min. at 40° C. Column 41: Positive control: MS-2 RNA; column 42; DNA marker; columns 43 to 45: MS-2 RNA after incubation with DTT-containing stabilizing solution (3-fold determination); columns 46 to 48: MS-2 RNA after incubation with stabilizing solution without DTT (3-fold determination).

Figure 5:
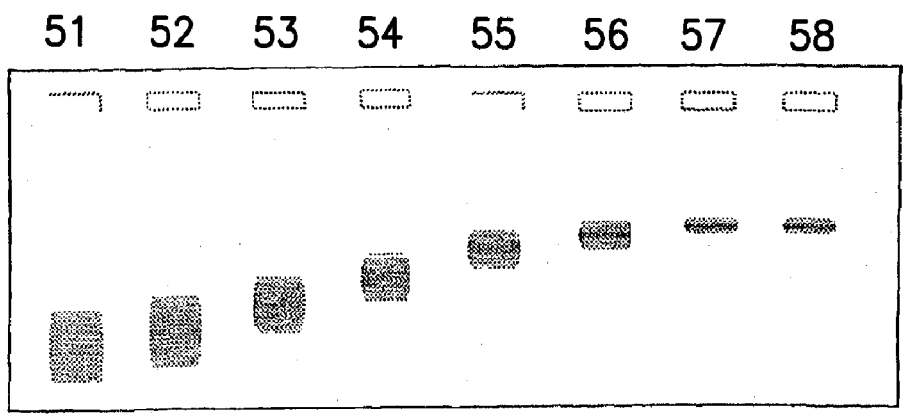

FIG. 5:
Graphical illustration of a gel analysis of MS2-RNA, which was isolated after incubation in serum/stabilizing solution for 3 days at 40° C. The guanidinium thiocyanate content (GTC content) of the stabilizing solution after the addition of serum, in which the RNA in question was incubated, is indicated in the corresponding column.

Column 51: 2.70 M GTC, column 52: 2.5 M GTC, column 53: 2.36 M GTC, column 54: 2.2 M GTC, column 55: 2.08 M GTC, column 56: 1.94 M GTC, column 57: 1.80 M GTC, column 58: 1.66 M GTC.

Figure 6:
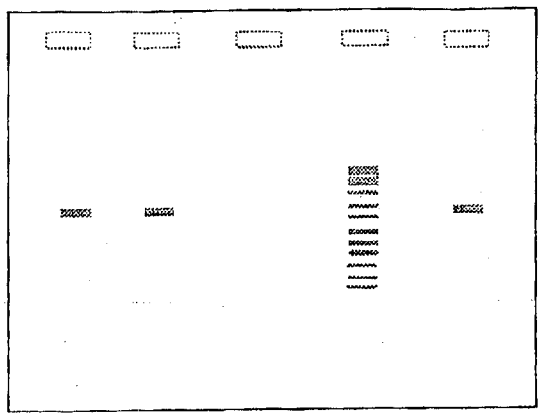

FIG. 6:
Graphical illustration of a gel analysis of the PCR amplification products of MS2-RNA, which was isolated in serum/stabilizing solution after incubation for 1 to 8 days at 40° C.

Column 61. amplification product of the RNA isolated after 1 day, column 62: amplification product of the RNA isolated after 8 days, column 63: DNA marker, column 64: MS2-RNA positive, control: 0.8 µg in 10 µl RT 1:50 diluted, 1 µl amplified.

Figure 7:
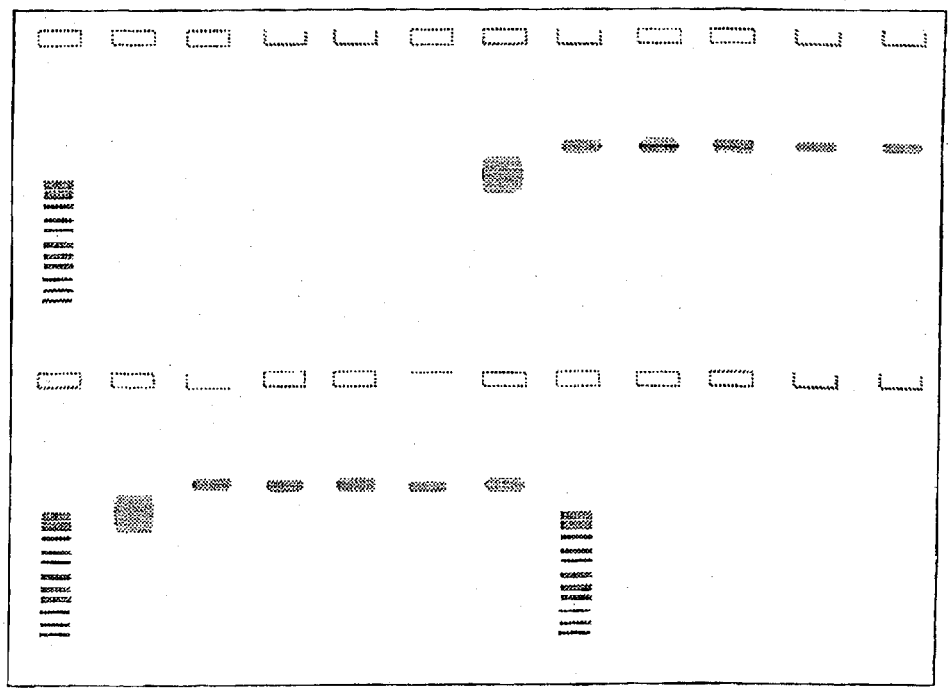

FIG. 7:
Graphical illustration of a gel analysis of isolated MS2-RNA after incubation for 6 (columns 72-712) and, respectively, 13 (columns 714-719) days at room temperature in serum/stabilizing solution. The pH-value obtained after mixing the serum and the stabilizing solution is indicated behind the columns in question.

Columns 71, 713, 720: DNA marker, column 72: pH 8.0, column 73: pH 7.7, column 74: pH 7.5, column 75: pH 7.35, column 76: pH 7.18, columns 77, 714: pH 7.07, columns 78, 715: pH 6.94, columns 79, 716: pH 6.8, columns 710, 717: pH 6.72, columns 711, 718: pH 6.68, columns 712, 719: pH 6.7. The stabilizing solution of the RNA in columns 712, 719 had the same pH-value as the ones of the RNA in column 711, however, contained 5M GTC instead of 4 M.

Figure 8:
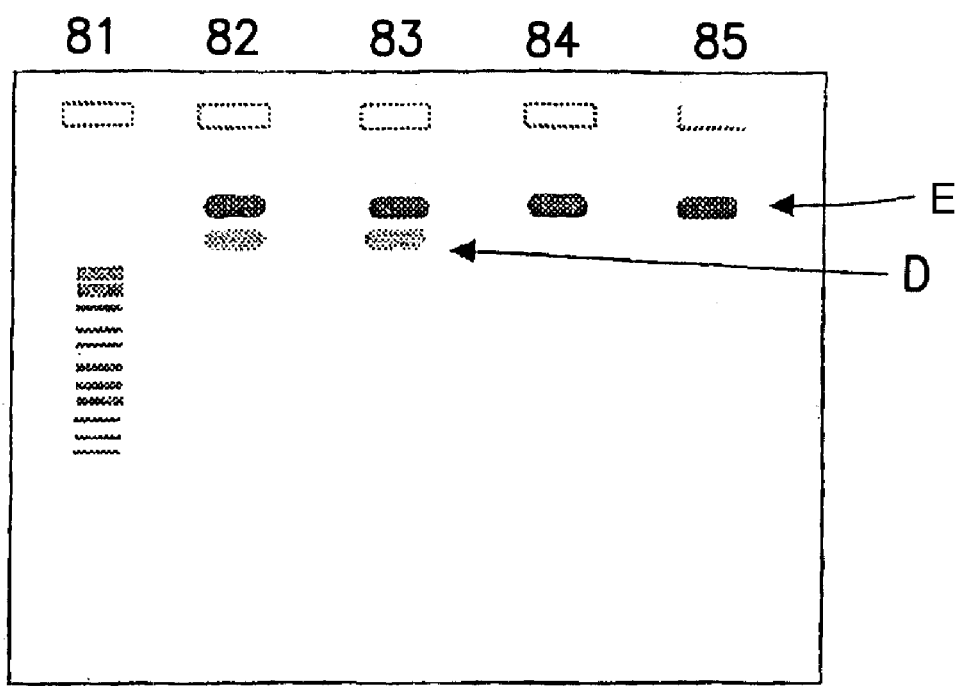

FIG. 8:
Graphical illustration of the proof of RNA and DNA in the standard agarose gel (1% agarose). Column 81: molecular weight marker, columns 82 to 84: isolated nucleic acids, column 82: nucleic acid from whole blood lysate containing MS2 RNA (7 days), column 83: nucleic acid from whole blood lysate containing MS2 RNA (0 days, control), column 84: nucleic acid from whole blood lysate (7 days), column 85: nucleic acid from whole blood lysate (0 days, control). The upper bands E show chromosomal DNA (clearly recognizable in all 4 samples), the lower bands D in columns 82 and 83 show the added and isolated MS2 RNA.

EXAMPLE 1

Blood Withdrawal System

According to a preferred embodiment the blood withdrawal system may be composed as follows (see FIG. 1): A small tube is filled with a defined volume of the nucleic-acid-stabilizing solution 1, is provided with a nucleic-acid-binding solid phase 3 and with a defined vacuum 2, and is then sealed with a septum 4. The septum 4 is constructed as to be compatible with the current sample withdrawal kit (cannula etc.) In the present example, 2.2 ml reagent were provided in advance, and the vacuum was adjusted to allow the inflow of 2.2 ml of blood exactly during the withdrawal of the sample. The nucleic acids contained in the inflowing blood stream were immediately transferred into a stable form.

General preliminary remark to the following examples.

If not mentioned otherwise, the nucleic-acid-stabilizing substance (N-sS) was composed as follows in all hereinafter described examples:: 45 mM tris, 5 M guanidinium thiocyanate, 0.8% (w/v) dithriothreitol, 18% (w/v) Triton-X-100, pH 6.0.

In all examples as described, the nucleic-acid-stabilizing substance was mixed with the sample in a ratio 1:1 (1 volume N-sS plus 1 volume sample material).

In all examples blood was stabilized by filling it directly, during the withdrawal, into the small tube containing N-sS.

EXAMPLE 2:

Stability of Nucleic Acid After Mixing Sample Material and N-sS.

Isolation of RNA and DNA of the Sample Lysate with Silica-derivatized Surfaces.

Material and Method:

The sample material for DNA and RNA isolation was used directly after the withdrawal, after storage for 6 days at 4° C. and after storage for 1 month at −20° C. The HighPure RNA Isolation Kit (Boehringer Mannheim, Cat.-No. 1828 665) was used for the isolation of RNA (FIG. 2). The provision in the enclosed information leaflet was modified as follows. A volume of 2.4 ml sample lysate was applied in 4 aliquots with 600 µl each onto the column, so that a total sample lysate of 2.4 ml lysate was applied. All other steps were carried out in correspondence with the enclosed, information leaflet. The RNA was eventually eluted with 100 µl elution buffer.

The QiaAmp Blood Kit (Qiagen-Cat.-No. 29104) was used for isolating DNA (FIG. 3). The standard procedure described in the enclosed information leaflet was modified in various points: 400 µl sample volume were directly applied onto the column, whereby the binding reagent contained in the kit was not used. 25 µl proteinase K stock solution were added, and the sample was incubated for 10 min. at room temperature. Thereafter, the column was placed in a collecting tank and centrifuged in accordance with the enclosed information leaflet. All additional steps were carried out in accordance with the description provided in the enclosed information leaflet, except for the use of ethanol. The elution volume was 200 µl.

EXAMPLE 3

Significance of Reducing Reagents (e.g. DTT) in the Stabilizing Solution for the Long-time Stabilization of RNA Material and Method:

Used Stabilizing Solution:

4.0 M GTC; 13.5% Triton-X-100; 45 mM tris/HCl; with or, respectively, without 120 mM DTT. 700 µl serum were mixed with 700 µl stabilizing solution. After an incubation for 2 min. 20 µl MS2-RNA (0.8 µg/µl from Roche Diagnostics) were added. The samples were incubated for 180 min. at 40° C. and thereafter applied in aliquots a 400 µl with the HighPure Total RNA Kit from Roche in accordance with experiment 1. The samples were eluted in 50 µl and frozen at −20° C. The analytics was effected with agarose gel (see FIG. 4).

Result: No long-time stabilization of RNA can be obtained without the addition of reducing reagents to the stabilizing solution.

EXAMPLE 4

Stability of MS2-RNA in Serum/Stabilizing Solution: Dependence on the GTC Concentration.

Material and Method

Used stabilizing solutions: 3-5 M GTC, 13.5% Triton-X-100; 50 mM DTT 42 mM tris/HCl;
pH of the solutions: approximately 4.0;
pH of the solutions after the addition of serum: approximately 6.7.

2 ml serum were mixed with 2.5 ml of the respective stabilizing solutions. After an incubation time of 2-5 min. 90 µl MS2-RNA (0.8 µg/µl from Roche) were added and incubated at 40° C. 400 µl sample were withdrawn at regular intervals and applied with the HighPure Total RNA Kit from Roche in accordance with experiment 1. The samples were eluted in 50 µl and frozen at −20° C. For analyzing the RNA integrity, 20 µl of the eluate were applied onto a 1.5% agarose gel (see FIG. 5). The RT-PCR-analytics was effected by means of AMV-RT and PCR. 10 µl of the eluates were subjected to reverse transcription by means of AMV-RT (Roche) and thereafter analyzed by means of quantitative PCR on the light cycler.

| Mixture for RT: (42° C. for 1 h) | 4.0 µl | AMV-RT buffer |
|---|---|---|
| | 2.0 µl | dNTP's (final concentration 10 mM) |
| | 0.5 µl | RNase inhibitor (Roche, 20 units) |
| | 1.0 µl | Primer 2827 (final concentration 1 µM) |
| | 1.9 µl | DMPC-water |
| | 0.6 µl | AMV-RT (Roche, 15 units) |
| | 10 µl | Template-RNA |
| | 20 µl | |

The PCR was carried out on the light cycler at an annealing temperature of 61° C. by the use of SYBR-Green as detection system All samples with a threshold cycle larger than 20 are considered to be negative, as the detected signal is exclusively ascribable to the formation of primer dimers. This can clearly be proved by the analysis of the melting curves on the light cycler (Roche). The RT product was diluted with 1:50 bidistillated water, and 1 µl thereof was used for a 10 µl PCR according to the following scheme:

| Mixture for PCR: | 1.6 µl | $MgCl_2$ (stock solution 25 mM) |
|---|---|---|
| | 5.9 µl | DMPC-water |
| | 0.25 µl | Primer 2827 (stock solution 20 mM) |

-continued

| | | |
|---|---|---|
| 0.25 µl | Primer 2335 (stock solution 20 mM) | |
| 1.0 µl | SYBR-Green-Mastermix (Roche) | |
| 1.0 µl | RT mixture | |
| 10 µl | | |

The amplification product of the PCR was completely applied onto a 2% agarose gel (see FIG. 6).

Result:

FIG. 5 shows the eluted MS2-RNA detected in the agarose gel after an incubation for 3 days at 40° C. Although all RNA samples can still be amplified and clearly be identified after 8 days at 40° C., clear differences of the RNA integrity in response to the GTC content can be recognized after 3 days already. Accordingly, a salt content lower than 2 M in the serum/stabilizing solution is advantageous for the integrity of the RNA.

Not shown is the fact that MS2-RNA is completely degraded by RNases already 2 min. after the addition to serum, so that RNA can no longer be identified. It could be proved by means of said example that the degradation of the RNA by the addition of stabilizing solution to the serum can clearly be delayed. MS2-RNA can be detected by PCR without any problems after 8 days at 40° C. in serum/stabilizing solution (see FIG. 6).

EXAMPLE 5

Stability of MS2-RNA in Serum/Stabilizing Solution: Dependence on the pH-value of the Sample Containing Stabilizing Solution.

Material and Method

| Used solution: | 4 M | GTC |
|---|---|---|
| | (5 M) | |
| | 14.4% | Triton-X-100 |
| | 50 mM | DTT |
| | 45 mM | tris HCl | pH after the addition of serum between 6.7 and 8.0

2.5 ml stabilizing solution were mixed with 2.0 ml serum. After the addition of 90 µl MS2 RNA (0.8 µg/ml, Roche) the samples were incubated at room temperature. The RNA from 500 µl sample were applied with the Roche viral RNA Kit according to example 4 at regular intervals and isolated in 50 µl elution buffer. 20 µl of the eluate were analyzed by means of agarose gel (see FIG. 7).

Result:

The pH of the serum/stabilizing solution and, thus, also the pH and buffer region of the stabilizing solution is decisive for the long-time stabilization of RNA. While, given a pH-value of 8.0, intact RNA could no longer be identified after 2 days already, intact RNA can still be identified after an incubation for 13 days at room temperature given a pH-range between 6.6 and 7.0. Apart from the pH-value, however, also an optimally adjusted GTC concentration is significant for the long-time stabilization of RNA (see example 4). The illustrated example makes it clear that a final concentration of GTC of 2.2 M GTC in the stabilized sample is better for a long-time stabilization than 2.8 M.

EXAMPLE 6

Stability of a Nucleic-acid-binding Surface in the Presence of a Stabilizing Solution Shown by the Use of Magnetic Particles Coated with Silica Material and Method

| Used solution: | 4.5 M | GTC |
|---|---|---|
| | 15% | Triton-X-100 |
| | 100 mM | DTT |
| | 50 mM | MES |

The magnetic particles coated with silica were taken from the mRNA Isolation Kit for Blood/Bone Marrow (Roche Molecular Biochemicals). The amount of particles used per ml was approximately 35 mg. The blood withdrawal system consisting of the small withdrawal tube, the stabilizing solution and the magnetic particles was stored for 14 days at room temperature. Afterwards, whole blood was withdrawn with said system. A freshly produced withdrawal system (small tube, stabilizing solution, magnetic particles) were used for control purposes. The isolation of the nucleic acids contained in the sample material was effected from both mixtures. The magnetic particles were separated with a magnet, the surplus was discarded. The particles were resuspended in 50% ethanol, 10 mM tris, pH 7.0, and washed with the same solution several times. The particles were finally heated in 10 mM tris/HCl pH 7.0 to 70° C., whereby the nucleic acid is set free from the magnetic particles. The particles were magnetically separated, and the surplus containing nucleic acid was analyzed in the standard agarose gel.

Result:

| | Sample (14 days, RT) | Control (0 days) |
|---|---|---|
| Nucleic acid provable in gel | + | + |

Table 1:

After a storage of 14 days the nucleic-acid-binding property of the solid phase has not changed. The sample as well as the control show the same nucleic-acid-binding properties.

EXAMPLE 7

Stability, Isolation and Proof of DNA and RNA After Storage for 7 Days with Simultaneous Binding to Magnetic Particles Coated with Silica Material and Method

| Used suspension: | 4.5 M | GTC |
|---|---|---|
| | 15% | Triton-X-100 |
| | 100 mM | DTT |
| | 50 mM | MES |
| | 35 mg/ml | particle |

Four blood withdrawal systems (small tubes) containing 1 ml of the above-described suspension were mixed with 1 ml whole blood. 25 μg MS2 RNA were additionally added into two of the small tubes (whole blood lysate). One small tube of each of the two mixtures (whole blood lysate+/−MS2 RNA) was applied immediately afterwards for the isolation of nucleic acids (performance see example 6). The other two small tubes were stored for 7 days at room temperature: The isolation of nucleic acids was carried out after said period of time. The elution volume amounted to 200 μl per 200 μl whole blood volume. The nucleic acids were analyzed in the standard agarose gel.

Result:

The stability of chromosomal DNA and MS2-RNA can be identified after storage for 7 days in the sample withdrawal system (solution, solid phase) (see FIG. 8).

The invention claimed is:

1. A process for isolating nucleic acid from a fluid sample comprising cells, the process comprising the steps of:
   providing a receptacle having an interior for receiving a sample, the interior comprising a nucleic acid-binding solid phase and a solution, wherein the interior is evacuated and wherein the solution comprises 1 to 8 M of guanidinium salt, a buffer, a reducing agent, and a detergent;
   drawing the fluid sample into the receptacle, wherein the solution causes lysis of the cells and stabilization of nucleic acids;
   storing the fluid sample in the receptacle for greater than one day, at temperatures comprising room temperature; and
   isolating nucleic acid from the stored fluid sample.

2. The process of claim 1, wherein the evacuation facilitates drawing of a defined volume of the fluid sample.

3. The process of claim 2, wherein the receptacle comprises a tube having an open end sealed by a septum.

4. The process of claim 3, wherein the defined volume is about 0.1 to about 4 times the volume of the solution.

5. The process of claim 2, wherein the buffer is effective, upon mixing with an amount of whole blood equal to the defined volume, to provide the resultant mixture with a pH between 4.0 and 7.5.

6. The process of claim 1, wherein the guanidinium salt is one or more salts selected from the group consisting of guanidinium thiocyanate and guanidinium chloride.

7. The process of claim 1, wherein the buffer is selected from the group consisting of: Tris (tris(hydroxymethyl) aminomethane), HEPES (4-(2-hydroxyethyl)-1-piperazineethanesulfonic acid), MOPS (4-morpholinepropanesulfonic acid), MES (4-morpholineethanesufonic acid), citrate and phosphate buffer.

8. The process of claim 1, wherein the reducing agent is selected from the group consisting of: dithiothreitol, β-mercaptoethanol and TCEP (tris(2-carboxyethyl)phosphine).

9. The process of claim 1, wherein the detergent is selected from the group consisting of: (polyethylene glycol tert-octylphenyl ether), (polyethylene glycol 4-nonylphenyl ether), Polydocanol (dodecyl polyethylene glycol ether) and (polyethylene glycol sorbitan monolaurate).

10. The process of claim 1, wherein the solid phase is separate from the receptacle and comprises fleece, filter, particles, gel, balls, plugs, rods, or mixtures thereof, or the solid phase is directly connected with the receptacle.

11. The process of claim 1, wherein the solution comprises 10 to 300 mM of the buffer.

12. The process of claim 1, wherein the isolating step is performed at least 3 days after the drawing step.

13. The process of claim 1, wherein the isolating step is performed at least 6 days after the drawing step.

14. The process of claim 1, wherein the isolating step is performed at least 8 days after the drawing step.

15. A process for isolating nucleic acid from a fluid sample comprising cells, the process comprising the steps of:
   providing a receptacle having an interior for receiving a sample, the interior comprising a nucleic acid-binding solid phase and a solution, wherein the interior is evacuated and wherein the solution comprises 1 to 8 M of guanidinium salt, a buffer, and a detergent;
   drawing the fluid sample into the receptacle, wherein the solution causes lysis of the cells and stabilization of nucleic acids;
   storing the fluid sample in the receptacle for greater than one day, at temperatures comprising room temperature; and
   isolating nucleic acid from the stored fluid sample.

16. The process of claim 15, wherein the evacuation facilitates drawing of a defined volume of the sample.

17. The process of claim 16, wherein the receptacle comprises a tube having an open end sealed by a septum.

18. The process of claim 16, wherein the buffer is effective, upon mixing with an amount of whole blood equal to the defined volume, to provide the resultant mixture with a pH between 4.0 and 7.5.

19. The process of claim 16, wherein the defined volume is about 0.1 to about 4 times the volume of the solution.

20. The process of claim 15, wherein the guanidinium salt is one or more salts selected from the group consisting of guanidinium thiocyanate and guanidinium chloride.

21. The process of claim 15, wherein the buffer is selected from the group consisting of: Tris (tris(hydroxymethyl) aminomethane), HEPES (4-(2-hydroxyethyl)-1-piperazineethanesulfonic acid), MOPS (4-morpholinepropanesulfonic acid), MES (4-morpholineethanesufonic acid), citrate and phosphate buffer.

22. The process of claim 15, wherein the detergent is selected from the group consisting of: polyethylene glycol tert-octylphenyl ether), (polyethylene glycol 4-nonylphenyl ether), Polydocanol (dodecyl polyethylene glycol ether) and (polyethylene glycol sorbitan monolaurate).

23. The process of claim 15, wherein the solid phase is separate from the receptacle and comprises fleece, filter, particles, gel, balls, plugs, rods, or mixtures thereof, or the solid phase is directly connected with the receptacle.

24. The process of claim 15, wherein the solution comprises 10 to 300 mM of the buffer.

25. The process of claim 15, wherein the isolating step is performed at least 3 days after the drawing step.

26. The process of claim 15, wherein the isolating step is performed at least 7 days after the drawing step.

27. The process of claim 15, wherein the isolating step is performed at least 14 days after the drawing step.

28. A process for isolating nucleic acid from a blood sample comprising cells, the process comprising the steps of:
   providing a receptacle having an interior for receiving a blood sample, the interior comprising a nucleic acid-binding solid phase and a solution, wherein the interior is evacuated and wherein the solution comprises 1 to 8 M of guanidinium salt, a buffer, and a detergent;

drawing the blood sample from a blood vessel directly into the interior, wherein the solution causes lysis of the cells and stabilization of nucleic acids;

storing the blood sample in the receptacle for greater than one day, at temperatures comprising room temperature; and isolating nucleic acid from the stored blood sample.

29. The process of claim 28, further comprising the step of engaging the vessel with a blood sampling accessory.

30. The process of claim 28, wherein the solution further comprises, a reducing agent.

31. The process of claim 30, wherein the solution comprises a single buffer, a single reducing agent and a single detergent.

* * * * *